(12) United States Patent
Ijuin

(10) Patent No.: US 9,255,298 B2
(45) Date of Patent: Feb. 9, 2016

(54) PROBE, AND POLYMORPHISM DETECTION METHOD USING THE SAME

(71) Applicant: Moeko Ijuin, Kyoto (JP)

(72) Inventor: Moeko Ijuin, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 157 days.

(21) Appl. No.: 13/863,877

(22) Filed: Apr. 16, 2013

(65) Prior Publication Data

US 2013/0280711 A1    Oct. 24, 2013

(30) Foreign Application Priority Data

Apr. 20, 2012 (JP) ................. 2012-096558
Apr. 10, 2013 (JP) ................. 2013-081858

(51) Int. Cl.
C12Q 1/68 (2006.01)
C12P 19/34 (2006.01)

(52) U.S. Cl.
CPC ........ *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS 8,232,051 B2 * 7/2012 Hirai et al. ............ 435/6.1

FOREIGN PATENT DOCUMENTS

| EP | 2036990 A1 | 3/2009 |
|----|------------|--------|
| JP | 2009-077712 A | 4/2009 |
| WO | 2005/059171 A1 | 6/2005 |
| WO | 2010/065626 A1 | 6/2010 |
| WO | 2011/071046 A1 | 6/2011 |

OTHER PUBLICATIONS

Nazarian et al., "Melanomas acquire resistance to B-RAF(V600E) inhibition by RTK or N-RAS upregulation," Nature, 468: 973-977 (2010).
Kumagai et al., "Clinical Implications of Pre-Operative Rapid BRAF Analysis for Papillary Thyroid Cancer," Endocrine Journal, 54: 399-405 (2007).
Cho et al., "Mutational Analysis of KRAS, BRAF, and TP53 Genes of Ovarian Serous Carcinomas in Korean Women," Yonsei Medical Journal, 50: 266-272 (2009).
Simi et al., "High-Resolution Melting Analysis for Rapid Detection of KRAS, BRAF, and PIK3CA Gene Mutations in Colorectal Cancer," American Journal of Clinical Pathology, 130: 247-253 (2008).
Rubinstein et al., "Incidence of the V600K mutation among melanoma patients with BRAF mutations, and potential therapeutic response to the specific BRAF inhibitor PLX4032," Journal of Translational Medicine, 8: 67 (2010).
Extended European Search Report issued in corresponding European Patent Application No. 13164586.3 dated Jul. 30, 2013.
Benlloch et al., "Detection of BRAF V600E Mutation in Colorectal Cancer," Journal of Molecular Diagnostics, 8: 540-543 (2006).
Watkins, Jr., et al., "Nearest-neighbor thermodynamics of deoxyinosine pairs in DNA duplexes," Nucleic Acids Research, 33: 6258-6267 (2005).
Office Action issued in corresponding European Patent Application No. 13164586.3 dated Mar. 17, 2015.

* cited by examiner

*Primary Examiner* — Jehanne Sitton
(74) *Attorney, Agent, or Firm* — Morgan, Lewis & Bockius LLP

(57) ABSTRACT

The present invention provides a probe for detecting a V600 polymorphism in the BRAF gene, which is (P1) a fluorescently labeled oligonucleotide which has an identity of at least 80% to a base sequence having a length of 10 to 50 bases including the 228th to 237th bases of the base sequence indicated in SEQ ID NO: 1, wherein the base corresponding to the 237th base is cytosine labeled with a fluorescent dye, the oligonucleotide recognizing a polymorphism in at least one of the 228th to 230th bases of the base sequence indicated in SEQ ID NO: 1 (with the proviso that the oligonucleotide is not the one indicated in SEQ ID NO: 7 or 19).

13 Claims, 4 Drawing Sheets

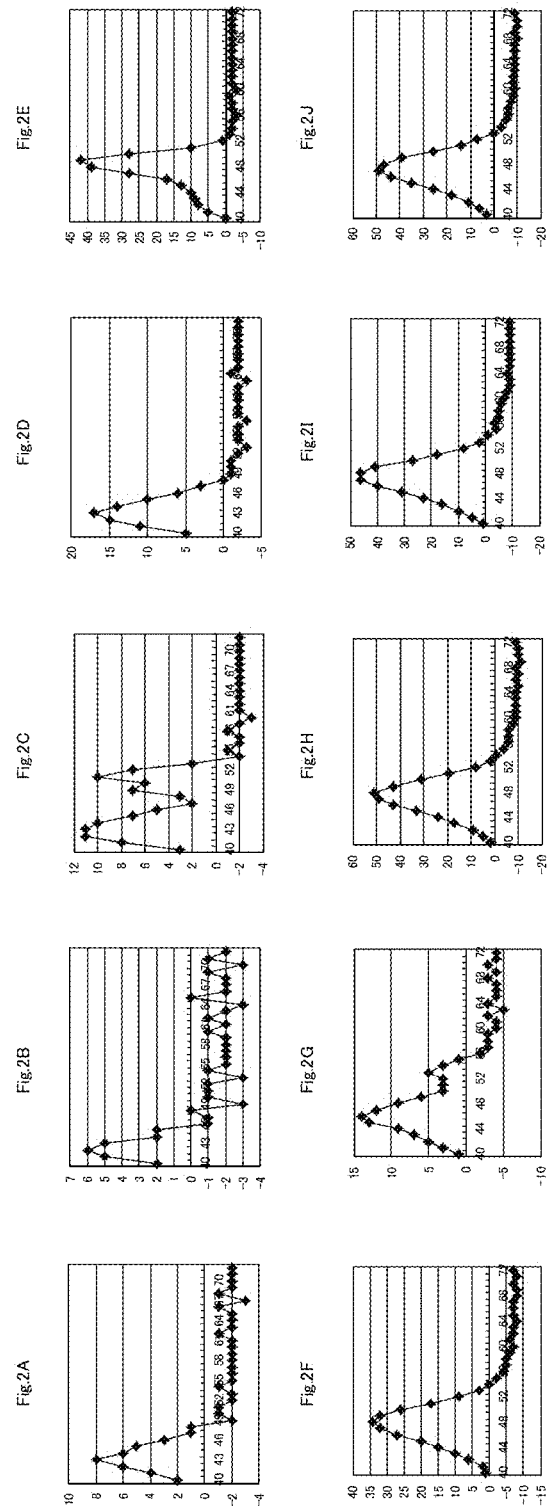

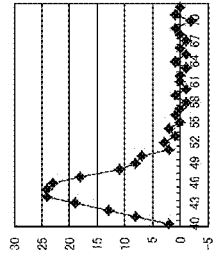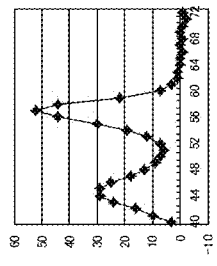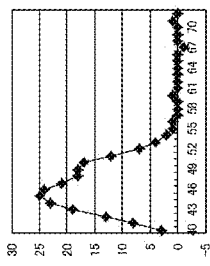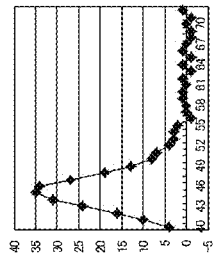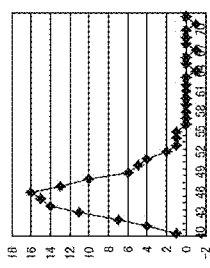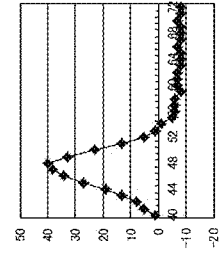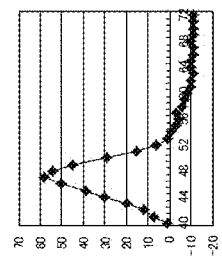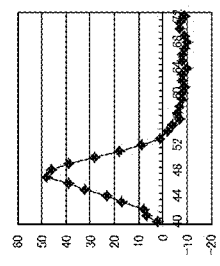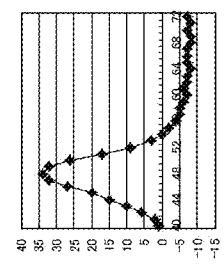

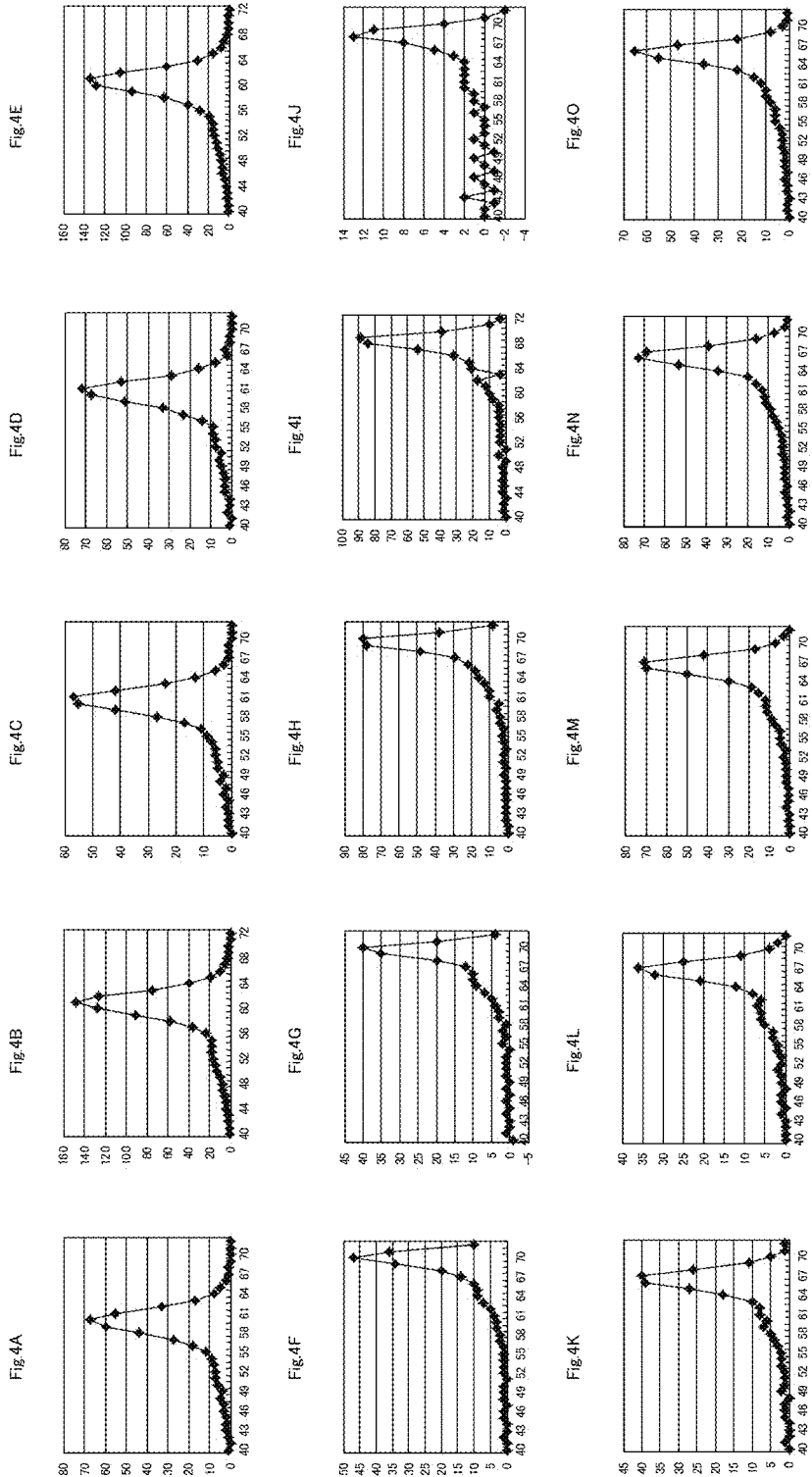

PROBE, AND POLYMORPHISM DETECTION METHOD USING THE SAME

The present application is related to Japanese Patent Application No. 2012-096558 filed on Apr. 20, 2012, and Japanese Patent Application No. 2013-081858 filed on Apr. 10, 2013. The contents of these applications are incorporated herein by reference in their entirety. All publications, patent applications, and technical standards mentioned in this specification are herein incorporated by reference to the same extent as if each individual publication, patent application, or technical standard was specifically and individually indicated to be incorporated by reference.

SEQUENCE LISTING SUBMISSION VIA EFS-WEB

A computer readable text file, entitled "SequenceListing.txt," created on or about Apr. 10, 2013 with a file size of about 6 kb contains the sequence listing for this application and is hereby incorporated by reference in its entirety.

BACKGROUND

1. Technical Field

The present invention relates to a probe for detecting a polymorphism, a method of detecting a polymorphism, a method of evaluating the efficacy of a drug, and a reagent kit for detecting a polymorphism.

2. Related Art

The BRAF gene encodes the BRAF protein which is involved in intracellular signaling and cell growth. It is known that the intracellular signaling pathway becomes constitutively activated when the BRAF gene undergoes mutation such that the 600th amino acid of the BRAF protein is mutated from valine (V) to glutamic acid (E). Such a BRAF-activated mutant is called "V600E" and is observed in about 7% of human malignant tumors and about 60% of malignant melanomas (see, for example, Nature. (2010) Dec. 16; 468 (7326): 973-7). Further, it has also been reported that advanced melanoma having a V600E mutation is effectively treated with, for example, the BRAF kinase inhibitor vemurafenib. When administering the BRAF kinase inhibitor vemurafenib, from the standpoints of the effectiveness and safety, it is necessary to detect the presence or absence of the V600E mutation in advance.

Methods have been developed by which the V600E mutation is measured accurately in a short time in an inexpensive and simple manner (see, for example, WO2011/071046 and Japanese Patent Application Laid-Open (JP-A) 2009-77712). In addition, methods of detecting a mutation in the BRAF gene using a PCR-RFLP method, a direct sequencing method, an HRMA method or the like are also known (see, for example, Endocr J. (2007) June 54(3): p. 399-405; Yonsei Med. J. (2009) April 30, 50(2): p. 266-'72; Am. J. Clin. Pathol. (2008) August, 130(2): p247-53).

At present, in addition to the V600E mutation, V600K, V600R and V600D mutations in which the 600th amino acid is mutated from valine to lysine (K), arginine (R) and aspartic acid (D), respectively, are known (see, for example, J. Transl. Med. (2010) Jul. 14, 8: p67). Further, V600G and V600M mutations in which the 600th amino acid is mutated to glycine (G) and methionine (M), respectively, are also known.

SUMMARY OF THE INVENTION

Problems to be Solved by the Invention

Until now, a method which is capable of simultaneously detecting two or more mutations other than V600E, which are V600K, V600R and V600D was not known.

Therefore, there exists a strong desire for further technological development to provide a method for easily detecting the V600E mutation along with other mutations (V600K, V600R and/or V600D) with high sensitivity.

An object of the present invention is to provide a polymorphism detection probe which allows a V600 polymorphism in the BRAF gene to be easily detected with high sensitivity. Another object of the present invention is to provide a polymorphism detection method utilizing the probe of the invention.

Means for Solving the Problems

The present invention is as follows.
<1> A probe for detecting a V600 polymorphism in the BRAF gene, which is the following P1 fluorescently labeled oligonucleotide:

(P1) an oligonucleotide which has an identity of at least 80% to a base sequence having a length of 10 to 50 bases including the 228th to the 237th bases of the base sequence indicated in SEQ ID NO:1, wherein the base corresponding to the 237th base is a cytosine labeled with a fluorescent dye, the oligonucleotide recognizing a polymorphism in at least one of the 228th to the 230th bases of the base sequence indicated in SEQ ID NO:1 (with the proviso that the oligonucleotide is not the one indicated in SEQ ID NO:7 or 19).

<2> The probe according to <1>, wherein the above-described P1 fluorescently labeled oligonucleotide is the following P1' fluorescently labeled oligonucleotide:

(P1') an oligonucleotide which has an identity of at least 80% to a base sequence having a length of 10 to 50 bases including the 228th to the 237th bases of the base sequence indicated in SEQ ID NO:1, wherein the base corresponding to the 237th base is cytosine; at least two of the 228th to the 230th bases of the base sequence indicated in SEQ ID NO:1 are different from the ones indicated in SEQ ID NO:1; and the above-described cytosine corresponding to the 237th base is labeled with a fluorescent dye.

<3> The probe according to <1> or <2>, wherein the above-described fluorescently labeled oligonucleotide has the base labeled with a fluorescent dye at any one of the first to the third positions from the 3'-end.

<4> The probe according to any one of <1> to <3>, wherein the above-described fluorescently labeled oligonucleotide has the base labeled with a fluorescent dye at the 3'-end.

<5> The probe according to any one of <1> to <4>, wherein the fluorescence intensity of the above-described fluorescently labeled oligonucleotide when hybridized to a target sequence is decreased or increased as compared to when not hybridized to the target sequence.

<6> The probe according to any one of <1> to <5>, wherein the fluorescence intensity of the above-described fluorescently labeled oligonucleotide when hybridized to the target sequence is decreased as compared to when not hybridized to the target sequence.

<7> The probe according to any one of <1> to <6>, wherein the above-described fluorescently labeled oligonucleotide has a length of 10 to 40 bases.
<8> The probe according to any one of <1> to <7>, wherein the above-described fluorescently labeled oligonucleotide has a length of 10 to 30 bases.
<9> The probe according to any one of <1> to <8>, which is a probe for melting curve analysis. This may alternatively be expressed as use of a probe according to any one of <1> to <8> for melting curve analysis.
<10> The probe according to any one of <1> to <9>, wherein the base corresponding to the 228th base of the base sequence indicated in SEQ ID NO:1 is guanine or adenine; the base corresponding to the 229th base of the base sequence indicated in SEQ ID NO:1 is adenine or guanine; and the base corresponding to the 230th base of the base sequence indicated in SEQ ID NO:1 is guanine or thymine.
<11> A method of detecting a polymorphism at the V600 locus of the BRAF gene, which includes using the probe according to any one of <1> to <10>.
<12> The method according to <11>, which includes the steps of:
(I) bringing the probe according to any one of <1> to <10> into contact with a single-stranded nucleic acid contained in a sample to hybridize the above-described fluorescently labeled oligonucleotide to the above-described single-stranded nucleic acid, thereby obtaining a hybrid;
(II) dissociating the above-described hybrid by changing the temperature of the sample containing the hybrid to measure the change in the fluorescence signal caused by dissociation of the hybrid;
(III) determining the Tm value, which is the dissociation temperature of the hybrid, based on the above-described change in the fluorescence signal; and
(IV) based on the above-described Tm value, detecting the presence of a mutation at the V600 locus of the BRAF gene.
<13> The method according to <11> or <12>, which further includes the step of amplifying the nucleic acid prior to or simultaneously with the above-described step (I) of obtaining a hybrid.
<14> A method of evaluating the efficacy of a drug, which includes the steps of:
detecting a mutation at the V600 locus of the BRAF gene by the method according to any one of <11> to <13>; and
determining (or predicting) tolerance to the drug or the efficacy of the drug based on the presence or absence of detected mutation. Said method may be performed on a sample from a subject (e.g. a human) in relation to whom the evaluation is to be made. A sample (as used herein) comprises nucleic acid (e.g. DNA) which may contain said mutation/polymorphism.
<15> A reagent for detecting a polymorphism, which includes the probe according to any one of <1> to <10>.
<16> A kit for detecting a polymorphism, which includes:
the probe according to any one of <1> to <10>; and
a primer capable of performing amplification using, as a template, a region of the base sequence indicated in SEQ ID NO:1 which contains a sequence to which the above-described probe hybridizes.
<17> The kit according to <16>, which further includes a primer capable of performing amplification using, as a template, a region having a length of 50 to 1,000 bases including the 228th to the 230th bases of the base sequence indicated in SEQ ID NO:1. The invention also extends to the use of the reagent or kit according to <15> to <17> or probe according to <1> to <10> for detecting said polymorphism in the BRAF gene.

Effects of the Invention

The present invention provides a polymorphism detection probe which allows a V600 polymorphism in the BRAF gene to be easily detected with high sensitivity, and a polymorphism detection method utilizing the probe.

BRIEF DESCRIPTION OF THE DRAWINGS

FIG. 2A to FIG. 2J are differential melting curves of samples according to Example 1 and Comparative Example 1 of the present invention.
FIG. 3A to FIG. 3J are differential melting curve of samples according to Example 2 and Comparative Example 1 of the present invention.
FIG. 4A to FIG. 4O are differential melting curves of samples according to Comparative Example 2 of the present invention.

DETAILED DESCRIPTION OF THE INVENTION

Figure 1A:
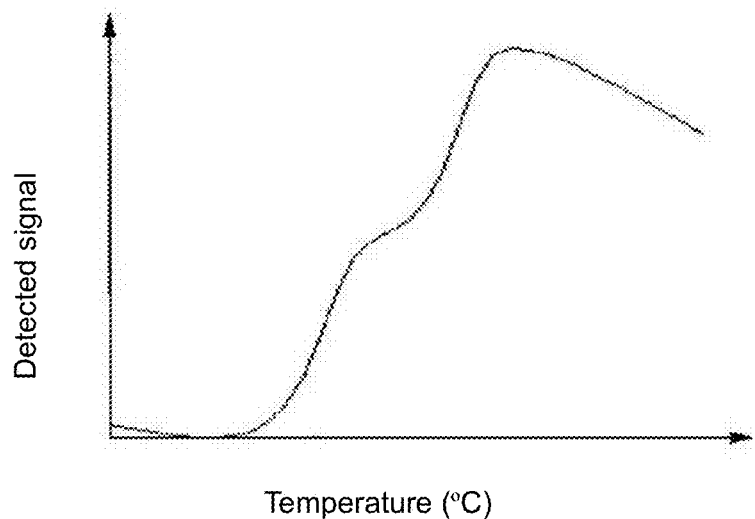
FIG. 1A is an example of a melting curve of a nucleic acid mixture.
Figure 1B:
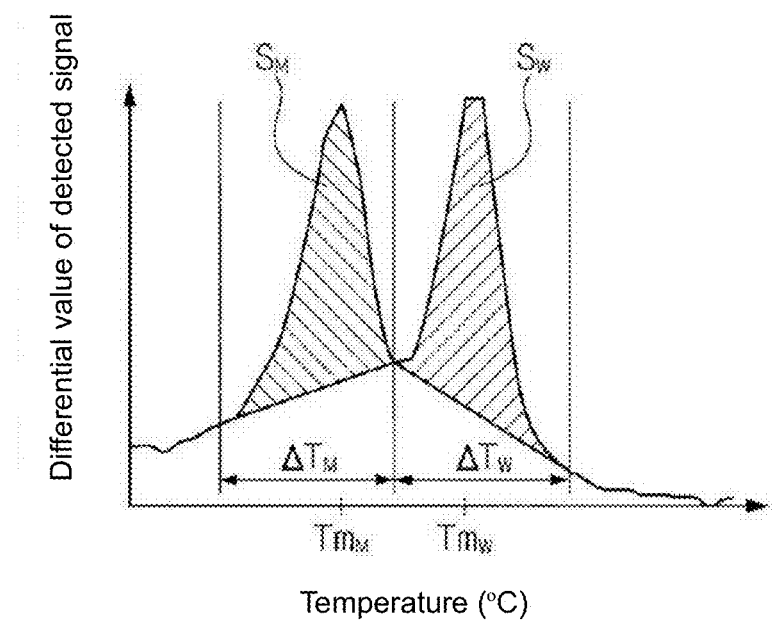
FIG. 1B is an example of a differential melting curve of a nucleic acid mixture.

The probe for detecting a V600 polymorphism in the BRAF gene according to the present invention (hereinafter, simply referred to as "the polymorphism detection probe") is a probe for detecting a V600 polymorphism in the BRAF gene which is the following P1 fluorescently labeled oligonucleotide:
(P1) an oligonucleotide which has an identity of at least 80% to a base sequence having a length of 10 to 50 bases including the 228th to 237th bases of the base sequence indicated in SEQ ID NO:1, wherein the base corresponding to the 237th base is a cytosine labeled with a fluorescent dye, the oligonucleotide recognizing a polymorphism in at least one of the 228th to the 230th bases of the base sequence indicated in SEQ ID NO:1 (with the proviso that the oligonucleotide is not the one indicated in SEQ ID NO:7 or 19).

The method of detecting a V600 polymorphism in the BRAF gene according to the present invention is a method which includes detecting a polymorphism in the BRAF gene using at least one probe for detecting a V600 polymorphism in the BRAF gene as described above.

The method of evaluating the efficacy of a drug according to the present invention is a method which includes detecting a V600 polymorphism in the BRAF gene by the above-described method of detecting a polymorphism in the BRAF gene, and evaluating (e.g. determining or predicting) tolerance to a drug or the efficacy of a drug based on the detected presence or absence of the polymorphism.

The reagent kit for detecting a polymorphism according to the present invention is a kit which contains the probe for detecting a V600 polymorphism in the BRAF gene.

The "BRAF gene" in the present invention is already known and the base sequence thereof is available as NCBI Accession No. NG007873.

In the present invention, the base sequence of SEQ ID NO:1 corresponds to the 176201st to 176700th bases of NCBI Accession No. NG007873 and it is constituted by base numbers 1 to 500 such that the base number 1 corresponds to the 176201st base of NCBI Accession No. NG007873.

In the present invention, the description of the base sequences of the sample nucleic acid to be detected in a sample and the polymorphism detection probe or primer shall also apply to complementary base sequences thereof, respectively, unless otherwise specified. Further, when the description of a particular base sequence is applied to a complementary base sequence thereof, the descriptions of base sequences recognized by the particular base sequence in the present invention should be applied provided that the recognition by the particular base sequence is replaced with recognition by a complementary base sequence of the particular base sequence, within a range of the common general technical knowledge of those skilled in the art.

In the present invention, the term "Tm value" is defined as the temperature at which a double-stranded nucleic acid dissociates (dissociation temperature: Tm), and is generally defined as the temperature at which the absorbance at 260 nm has increased by 50% of the total increase in absorbance resulting from complete dissociation of the double-stranded nucleic acid. More specifically, when a solution containing a double-stranded nucleic acid such as a double-stranded DNA is heated, the absorbance at 260 nm of the double-stranded nucleic acid gradually increases. This is because the hydrogen bonds between both strands of the double-stranded DNA are broken by heating, thereby dissociating the double-stranded DNA into single-stranded DNA (melting of DNA). When the double-stranded DNA has completely dissociated into single-stranded DNA, the single-stranded DNA exhibit an absorbance that is about 1.5 times the absorbance at the time of the initiation of the heating (i.e., the absorbance when the entire DNA is in the form of a double-stranded DNA), which serves as an indicator of the completion of the melting. The Tm value is defined based on this phenomenon.

In the present specification, the scope of the term "process" or "step" includes not only a discrete process/step, but also a process/step that cannot be clearly distinguished from another process/step as long as the expected effect of the process/step of interest is achieved.

In the present specification, any numerical range expressed using "to" refers to a range including the numerical values before and after "to" as the minimum and maximum values, respectively.

In the case in which the amount of a component that may be included in the composition is indicated in the present invention, when there are multiple substances corresponding to the component in the composition, the indicated amount means the total amount of the multiple substances present in the composition, unless specifically stated otherwise.

In the present invention, when the phrase "the first to third bases from the 3' end" is used in connection with an oligonucleotide sequence, it is assumed that the base at the 3' end of the oligonucleotide chain is the first base from the 3' end.

The present invention is described below.

<Probe for Detecting V600 Polymorphism in BRAF Gene>

The probe for detecting a V600 polymorphism in the BRAF gene according to the present invention (hereinafter, simply referred to as "the polymorphism detection probe") is a probe for detecting a V600 polymorphism in the BRAF gene which is the following P1 fluorescently labeled oligonucleotide:

(P1) an oligonucleotide which has an identity of at least 80% to a base sequence having a length of 10 to 50 bases including the 228th to 237th bases of the base sequence indicated in SEQ ID NO:1, wherein the base corresponding to the 237th base is a cytosine labeled with a fluorescent dye, the oligonucleotide recognizing a polymorphism in at least one of the 228th to 230th bases of the base sequence indicated in SEQ ID NO:1 (with the proviso that the oligonucleotide is not the one indicated in SEQ ID NO:7 or 19).

The above-described P1 fluorescently labeled oligonucleotide of the present invention is a probe capable of detecting a polymorphism of at least one base selected from the group consisting of the 228th to the 230 bases of the base sequence indicated in SEQ ID NO:1.

More specifically, the above-described P1 fluorescently labeled oligonucleotide of the present invention is a sequence which includes the bases corresponding to the 228th to the 237th bases of the sequence indicated in SEQ ID NO:1.

In addition to the requirement that the base corresponding to the 237th base of the base sequence indicated in SEQ ID NO:1 is cytosine (C), the P1 fluorescently labeled oligonucleotide of the present invention is required to have an identity of at least 80% to a base sequence having a length of 10 to 50 bases including the 228th to the 237th bases of the base sequence indicated in SEQ ID NO:1. It is noted here that "a base sequence having a length of 10 to 50 bases including the 228th to the 237th bases of the base sequence indicated in SEQ ID NO:1" may be hereinafter also referred to as a "specific partial base sequence" and said 10 to 50 bases are consecutive bases of SEQ ID No. 1 which include the 228th to 237th bases of the base sequence.

From the standpoint of the detection sensitivity, such a fluorescently labeled oligonucleotide may also exhibit an identity of not less than 85%, not less than 90%, not less than 95%, not less than 96%, not less than 97%, not less than 98% or not less than 99%.

When the identity between the above-described P1 fluorescently labeled oligonucleotide of the present invention and the base sequence having the same bases as SEQ ID NO:1 except that the base corresponding to the 237th base is C (cytosine) is less than 80%, the detection sensitivity for a sample nucleic acid containing a mutant-type BRAF gene becomes low.

Alternatively, the above-described P1 fluorescently labeled oligonucleotide of the present invention may also be an oligonucleotide (P1') having an identity of at least 80% to the above-described specific partial base sequence, in which the base corresponding to the 237th base is cytosine; at least two of the bases corresponding to the 228th to the 230th bases of the base sequence indicated in SEQ ID NO:1 are different from the ones indicated in SEQ ID NO:1; and the above-described cytosine corresponding to the 237th base is labeled with a fluorescent dye.

By being constituted such that at least two of the 228th to the 230th bases of the base sequence indicated in SEQ ID NO:1 are different in the oligonucleotide from the ones indicated in SEQ ID NO:1, the P1' fluorescently labeled oligonucleotide tends to have an increased detection sensitivity for a sample nucleic acid containing a mutant-type BRAF gene.

In cases where at least two of the bases corresponding to the 228th to the 230th bases of the base sequence indicated in SEQ ID NO:1 are different from the ones in SEQ ID NO:1, the at least two bases may be, for example, two or more bases selected from the group consisting of the following (1) to (3):

(1) the base corresponding to the 228th base of the base sequence indicated in SEQ ID NO:1, which is guanine or adenine;

(2) the base corresponding to the 229th base of the base sequence indicated in SEQ ID NO:1, which is adenine or guanine; and (3) the base corresponding to the 230th base of the base sequence indicated in SEQ ID NO:1, which is guanine or thymine.

Further, as a specific combination of the at least two bases, examples thereof include those cases where the bases corresponding to the 228th, the 229th and the 230th bases are, respectively, adenine, adenine and guanine; adenine, adenine and thymine; adenine, guanine and thymine; adenine, guanine and guanine; guanine, adenine and thymine; and guanine, guanine and thymine.

From the standpoint of simultaneously detecting two or more bases, as the combination of the at least two bases, the bases corresponding to the 228th, the 229th and the 230th bases may be, respectively, adenine, adenine and guanine; adenine, guanine and guanine; or guanine, adenine and thymine.

Further, the above-described P1 or P1' fluorescently labeled oligonucleotide of the present invention may also be a fluorescently labeled oligonucleotide in which the base corresponding to the 228th base of the base sequence indicated in SEQ ID NO:1 is guanine or adenine; the base corresponding to the 229th base of the base sequence indicated in SEQ ID NO:1 is adenine or guanine; and the base corresponding to the 230th base of the base sequence indicated in SEQ ID NO:1 is guanine or thymine.

Such a fluorescently labeled oligonucleotide exhibits a large difference in the Tm value between a wild-type and a mutant-type; therefore, a test using the fluorescently labeled oligonucleotide tends to accurately detect a mutation and is thus highly reliable and that the test can detect a mutation in a sample with high sensitivity.

In the present invention, the above-described P1 or P1' fluorescently labeled oligonucleotide also encompasses a fluorescently labeled oligonucleotide which hybridizes, under stringent conditions, to the complementary strand of a base sequence having the same bases as the above-described specific partial base sequence except that the base corresponding to the 237th base is C (cytosine).

The hybridization may be carried out (under stringent conditions) according to a known method or a method corresponding thereto, such as a method as described in Molecular Cloning 3rd (J. Sambrook et al., Cold Spring Harbor Lab. Press, 2001). This document is incorporated herein by reference.

The term "stringent conditions" means conditions in which specific hybrids are formed, but non-specific hybrids are not formed. Typical examples of the stringent conditions include, for example, conditions in which the hybridization is carried out at a potassium concentration from about 25 mM (e.g. 25 mM) to about 50 mM (e.g. 50 mM) and a magnesium concentration from about 1.0 mM (e.g. 1.0 mM) to about 5.0 mM (e.g. 5.0 mM). One example of the conditions of the present invention is conditions in which the hybridization is carried out in Tris-HCl (pH 8.6), 25 mM KCl, and 1.5 mM $MgCl_2$, but examples of the conditions of the present invention are not limited thereto. Other examples of the stringent conditions are described in Molecular Cloning 3rd (J. Sambrook et al., Cold Spring Harbor Lab. Press, 2001). This document is incorporated herein by reference. Those skilled in the art may readily choose such conditions by changing the hybridization reaction and/or the salt concentration of the hybridization reaction solution.

Furthermore, the P1 or P1' fluorescently labeled oligonucleotides of the present invention encompasses a fluorescently labeled oligonucleotide having a sequence wherein a base(s) has been inserted to, deleted from and/or substituted in P1 or P1' fluorescently labeled oligonucleotides.

The fluorescently labeled oligonucleotide having a sequence wherein a base(s) has been inserted, deleted and/or substituted is not particularly limited, as long as the oligonucleotide exhibits an effect similar to that of P1 or P1' fluorescently labeled oligonucleotides; and, in cases where a base(s) has been inserted, deleted and/or substituted, the position(s) of the insertion(s), deletion(s) and/or substitution(s) is not particularly limited. The number of bases that has been inserted, deleted and/or substituted may be, for example, 1 base, or 2 or more bases, such as from 1 base to 10 bases and from 1 base to 5 bases, although this may vary depending on the total length of the fluorescently labeled oligonucleotide.

Among those fluorescently labeled oligonucleotides having a sequence wherein a base(s) has been inserted, deleted and/or substituted, the above-described P1 or P1' fluorescently labeled oligonucleotide of the present invention may be, for example, one having a sequence wherein a base(s) has been substituted. The position of the substitution is not particularly limited. From the standpoint of the detection sensitivity, for example, a base which is not the 231st to the 237th bases of the sequence indicated in SEQ ID NO:1 may be substituted. The number of bases that are substituted may be, for example, 1 base, or 2 or more bases. Although the number of bases that are substituted varies depending on the total length of the fluorescently labeled oligonucleotide, it is, for example, 1 to 5 bases or 1 to 3 bases.

The oligonucleotides in the above-described fluorescently labeled oligonucleotides also encompass oligonucleotides as well as modified oligonucleotides.

Examples of a structural unit of the above-described oligonucleotide include ribonucleotides, deoxyribonucleotides and artificial nucleic acids. Examples of the artificial nucleic acids include DNAs, RNAs, LNAs (Locked Nucleic Acids) which are RNA analogues, PNAs (Peptide Nucleic Acids) which are peptide nucleic acids, BNAs (Bridged Nucleic Acids) which are cross-linked nucleic acids, and the like.

The above-described oligonucleotides may be constituted by one or multiple types of the structural units described in the above.

The above-described P1 and P1' fluorescently labeled oligonucleotides of the present invention are required to have a length of 10 mer to 50 mer. When the P1 and P1' fluorescently labeled oligonucleotides have a length shorter than 10 mer or longer than 50 mer, the sensitivity for detecting a polymorphism in the BRAF gene is decreased.

Further, the P1 and P1' fluorescently labeled oligonucleotides of the present invention may have a length of 10 mer to 50 mer, 10 mer to 40 mer, or 10 mer to 30 mer. By setting the length in the range of 10 mer to 50 mer, for example, the detection sensitivity tends to be increased.

By changing the base lengths of the P1 and P1' fluorescently labeled oligonucleotides, the Tm value, which is the dissociation temperature of a hybrid formed between the fluorescently labeled oligonucleotides and their respective complementary strands (target sequences), can be adjusted to a desired value.

Examples of the base sequence of the P1 or P1' fluorescently labeled oligonucleotide of the present invention are shown in Table 1 below, but the present invention is not limited to these.

It is noted here that, in Table 1, the bases corresponding to the 228th to the 230th bases of the base sequence shown in SEQ ID NO:1 are each indicated with a capital letter. In addition, Table 1 also shows the Tm values of hybrids that form between each fluorescently labeled oligonucleotide and an oligonucleotide in which the bases corresponding to the 228th, the 229th and the 230th of SEQ ID NO:1 are, respectively, adenine, adenine and guanine; adenine, guanine and guanine; or guanine, adenine and thymine.

The Tm values were calculated using MeltCalc© 99 FREE (http://www.meltcalc.com/) and under the set conditions of: Oligoconc. [μM] of 0.2 and Na eq. [mM] of 50.

TABLE 1

| sequence (5'→3') | mer | Tm | | | | Δ* | | | SEQ ID NO: |
| --- | --- | --- | --- | --- | --- | --- | --- | --- | --- |
| | | WT GTG | V600K AAG | V600R AGG | V600D GAT | V600K AAG | V600R AGG | V600D GAT | |
| gtctagctacaAATaaatctc | 21 | 30.4 | 39.1 | 34.7 | 36.8 | 8.7 | 4.3 | 6.4 | 8 |
| tagctacaAGGaaatctc | 18 | 30.3 | 35.7 | 44.1 | 24.2 | 5.4 | 13.9 | 6.1 | 9 |
| aggtgattttggtctagctacaAATaaatctc | 32 | 49.8 | 53.6 | 51.9 | 52.8 | 3.8 | 2.0 | 3.0 | 10 |
| ctacaAATaaatctc | 15 | 2.5 | 21.0 | 11.2 | 15.5 | 18.5 | 8.7 | 13.0 | 11 |
| tgattttggtctagctacaAGGaaatctc | 29 | 49.8 | 52.3 | 56.7 | 46.8 | 2.4 | 6.9 | 3.1 | 12 |
| ctacaAGGaaatctc | 15 | 18.6 | 26.0 | 36.9 | 10.6 | 7.4 | 18.3 | 8.0 | 13 |

*Δ represents a difference in the Tm value between mt (mutant-type) and WT (wild-type).

In the present invention, the difference between the Tm value measured when the above-described P1 or P1' fluorescently labeled oligonucleotide is hybridized with a DNA having a base sequence complementary thereto (Tm (V600K, V600R or V600D) in Table 1) and the Tm value measured when a base sequence corresponding to the 228th to the 230th bases of the base sequence indicated in SEQ ID NO:1 is hybridized with a DNA having a sequence complementary thereto (Tm (WT) in Table 1) is, for example, not less than 3° C. When the above-described difference in the Tm value is 3° C. or larger, for example, a mutation in the 228th to the 230th bases of the base sequence indicated in SEQ ID NO:1 can be detected with a higher sensitivity.

Further, the above-described difference in the Tm value may be, for example, not less than 3° C., not less than 5° C. or not less than 7° C.

Examples of a method of increasing the difference in the Tm value include a method by which a probe is allowed to contain a base which mismatches with a base sequence corresponding to a region to which the probe hybridizes. Specific examples include those methods described in Nature Biotech (1997) vol. 15, pp. 331-335 and the like.

Further, the P1 or P1' fluorescently labeled oligonucleotide of the present invention needs to be labeled with a fluorescent dye at its base corresponding to the 237th base (cytosine).

In the P1 or P1' fluorescently labeled oligonucleotide, the fluorescently labeled base corresponding to the 237th base may exist at a position of any one of the 1st to 3rd positions from the 3' end of the P1 or P1' fluorescently labeled oligonucleotide. Alternatively, the fluorescently labeled base may exist at the 3' end of the P1 or P1' fluorescently labeled oligonucleotide. Thereby, for example, the sensitivity for detecting a polymorphism is further improved. In addition, the P1 or P1' fluorescently labeled oligonucleotide may be obtained with good productivity (or efficacy).

The above described fluorescently labeled oligonucleotide of the present invention may be a fluorescently labeled oligonucleotide in which the fluorescence intensity at the time when the oligonucleotide is hybridized to a sequence including the 228th to the 230th bases of the base sequence indicated in SEQ ID NO:1 (target sequence) is decreased (quenched) or increased as compared to the fluorescence intensity at the time when the oligonucleotide is not hybridized to the target sequence. In particular, the fluorescently labeled oligonucleotide of the present invention may be a fluorescently labeled oligonucleotide in which the fluorescence intensity at the time when the oligonucleotide is hybridized to its target sequence is decreased as compared to the fluorescence intensity at the time when the oligonucleotide is not hybridized to its target sequence.

A probe that uses the "fluorescence quenching phenomenon" as described above is generally referred to as a guanine quenching probe, and it is known as Q PROBE®. Among such probes, an oligonucleotide which has been designed so that its 3' or 5' end is a cytosine (C) and which has been labeled with a fluorescent dye so that the fluorescence emission is reduced when the C at the 3' or 5' end comes into proximity with a guanine (G) is especially preferable. By using such a probe, the hybridization and dissociation of the probe may be readily checked by the change in its signal.

A known detection method other than the detection method using a Q PROBE® may also be applied. Examples of such a detection method include a TAQ-MAN probe method, a hybridization probe method, a molecular beacon method, and a MGB probe method.

The fluorescent dye is not particularly limited, and examples of the fluorescent dye include fluorescein, phosphor, rhodamine and polymethine dye derivatives. Examples of commercially available products of such fluorescent dyes include Pacific Blue, BODIPY FL, FluorePrime, Fluoredite, FAM, Cy3 and Cy5, and TAMRA.

The detection conditions of the fluorescently-labeled oligonucleotide are not particularly limited, and may be decided, as appropriate, in accordance with the fluorescent dye to be used. For example, Pacific Blue can be detected at a detection wavelength from 445 nm to 480 nm, TAMRA can be detected at a detection wavelength from 585 nm to 700 nm, and BODIPY FL can be detected at a detection wavelength from 520 nm to 555 nm.

By using a probe having such a fluorescent dye, hybridization and dissociation of the probe can be readily confirmed based on the change in fluorescence signal therefrom. Attachment of a fluorescent dye to the oligonucleotide may be carried out according to an ordinary method, such as a method described in JP-A No. 2002-119291.

It should be noted that, in the present invention, the same fluorescent dye may be used, or alternatively, different fluorescent dyes may be used to label one or more of the oligonucleotides.

In addition, the fluorescently-labeled oligonucleotide may have, for example, a phosphate group added to its 3' end. Addition of a phosphate group to the 3' end of the fluorescently-labeled oligonucleotide suppresses elongation of the probe itself by a gene amplification reaction. As described below, DNA in which the presence or absence of a mutation should be detected (target DNA) may be prepared using a gene amplification method such as PCR. When the fluorescently-labeled oligonucleotide that has a phosphate group added to its 3' end is used, the amplification reaction can be carried out even in the presence of the oligonucleotide in the reaction solution of the amplification reaction.

A similar effect can be obtained also by adding a labeling substance (a fluorescent dye) as described above to the 3' end.

Specific examples of an oligonucleotide having the above-described base sequence in which the C at the 3'-end is labeled with a fluorescent dye are shown below (The bases indicated with a capital letter represent the positions of mutation, and "(PB)", "(FL)" and "(TAMRA)" correspond to the respective fluorescent dyes described in the above). However, the fluorescently labeled oligonucleotide of the present invention is not restricted to the following oligonucleotides.

TABLE 2

| name | sequence(5'→3') | mer | SEQ ID NO: |
|---|---|---|---|
| 3PB-BRAF600KDmt-F1-21 | gtctagctacaAATaaatctc-(PB) | 21 | 8 |
| 3FL-BRAF600Rmt-F1-18 | tagctacaAGGaaatctc-(FL) | 18 | 9 |
| 3T-BRAF600KDmt-F1-32 | aggtgattttggtctagctacaAATaaatc-(TAMRA)-tc | 32 | 10 |
| 35T-BRAF600KDmt-F1-15 | (TAMRA)-ctacaAATaaatctc-(TAMRA) | 15 | 11 |
| 3T-BRAF600Rmt-F1-29 | tgattttggtctagctacaAGGaaatctc-(TAMRA) | 29 | 12 |
| 35T-BRAF600Rmt-F1-15 | (TAMRA)-ctacaAGGaaatctc-(TAMRA) | 15 | 13 |

The above-described P1 and P1' fluorescently labeled oligonucleotides may be used as a probe for detecting a V600 polymorphism in the BRAF gene.

In addition, the above-described P1 and P1' fluorescently labeled oligonucleotides may be used as a probe for melting curve analysis.

Further, the above-described P1 and P1' fluorescently labeled oligonucleotides may also be used in a reagent for detecting a polymorphism. By this, the reagent for detecting a polymorphism according to the present invention is capable of easily detecting a polymorphism in the bases corresponding to the 228th to the 230th bases of the base sequence indicated in SEQ ID NO:1 with high sensitivity.

The P1 and P1' fluorescently labeled oligonucleotide according to the present invention may be produced according to a conventional method known as a method for synthesizing an oligonucleotide, such as a method as described in JP-A No. 2002-119291, except that bases are used so that the base corresponding to the 237th base in the base sequence indicated in SEQ ID NO:1 is a cytosine and the base corresponding to the 237th base is labeled with a fluorescent dye.

<Primer>

In the below-described method of detecting a polymorphism in the BRAF gene, primers are used to amplify a sequence having a BRAF gene polymorphism to be detected by a PCR method.

The primers that may be used in the present invention are not particularly restricted as long as they are capable of amplifying a nucleic acid containing the bases corresponding to the 228th to the 230th bases of the base sequence indicated in SEQ ID NO:1, which is the site of a BRAF gene polymorphism to be detected.

The primer to be applied to the PCR method is not particularly limited, as long as it is capable of amplifying a region to which the probe of the present invention may be hybridized. Such a primer may be designed based on the base sequences indicated in SEQ ID NO:1 by those skilled in the art. The length and Tm value of the primer may be a length from 12 mer to 40 mer and a value from 40° C. to 70° C., or a length from 16 mer to 30 mer and a value from 55° C. to 60° C.

The lengths of individual primers in a primer set do not need to be the same, although the Tm values of these primers are preferably approximately the same (or the difference between the Tm values of these primers is preferably within 5° C.).

Examples of the primers that may be used for amplifying a base sequence containing a region to which the polymorphism detection probe according to the present invention used in the method of detecting a polymorphism according to the present invention hybridizes are shown below. It is noted here that the following examples are provided for illustrative purposes only and that, therefore, the present invention is not restricted thereto.

The above-described primer may be (P2) an oligonucleotide which has an identity of at least 80% to a base sequence having a length of 30 to 40 bases including the 115th to the 144th bases of the base sequence indicated in SEQ ID NO:1 and amplifies a region containing the bases corresponding to the 228th to the 230th bases of the base sequence indicated in SEQ ID NO:1. Further, the above-described P2 oligonucleotide may also be an oligonucleotide which hybridizes, under stringent conditions, to a complementary strand of a base sequence having a length of 30 to 40 bases including the 115th to the 144th bases of the base sequence indicated in SEQ ID NO:1. The above-described P2 oligonucleotide may also be an oligonucleotide having a sequence in which a base(s) is/are inserted, deleted and/or substituted in the P2 oligonucleotide.

Alternatively, the above-described primer may be the following primer. That is, the above-described primer may also be (P3) an oligonucleotide which has an identity of at least 80% to a complementary strand of a base sequence having a length of 22 to 40 bases including the 239th to the 260th bases of the base sequence indicated in SEQ ID NO:1 and amplifies a region containing the bases corresponding to the 228th to the 230th bases of the base sequence indicated in SEQ ID NO:1. Further, the above-described P3 oligonucleotide may also be an oligonucleotide which hybridizes, under stringent conditions, to a base sequence having a length of 22 to 40 bases including the 239th to the 260th bases of the base sequence indicated in SEQ ID NO:1. The above-described P3 oligonucleotide may also be an oligonucleotide having a sequence in which a base(s) is/are inserted, deleted and/or substituted in the P3 oligonucleotide.

As for the method of performing hybridization, hybridization may be performed in accordance with the method described in the above section of probes and, as the "stringent conditions", the same conditions described in the above section of probes are applicable. Further, also for the range of the identity and the conditions of insertion, deletion and/or substitution, the same range/matters described in the above section of probes are applicable.

Examples of primers that can be used in the method of detecting a polymorphism according to the present invention to amplify a region containing the bases corresponding to the 228th to the 230th bases of the base sequence indicated in SEQ ID NO:1 are shown below.

TABLE 3

| name | sequence(5'→3') | mer | SEQ ID NO: |
|---|---|---|---|
| BRAF-F3 | tgcttgctctgataggaaaatgagatctac | 30 | 17 |
| BRAF-R5 | aaactgatgggacccactccat | 22 | 18 |

In order to detect a polymorphism in the bases corresponding to the 228th to the 230th bases of the base sequence indicated in SEQ ID NO:1, for example, the above-described P2 and P3 oligonucleotides may be used as a set of paired primers.

The method of detecting a polymorphism is not particularly limited, as long as it is a method in which a fluorescently labeled oligonucleotide as described above is used as a probe. As an example of the polymorphism detection method in which a fluorescently labeled oligonucleotide as described above is used as a probe, a method of detecting a polymorphism using Tm analysis is described below.

<Polymorphism Detection Method>

The method of detecting a V600 polymorphism in the BRAF gene according to the present invention is a method of detecting a V600 polymorphism in the BRAF gene which includes detecting a V600 polymorphism in the BRAF gene by using at least one probe for detecting a V600 polymorphism in the BRAF gene as described above.

The method of detecting a polymorphism of the present invention may include at least one probe for detecting a polymorphism as described above, and this may make it possible to detect a V600 polymorphism(s) in the BRAF gene easily and with high sensitivity.

In addition, the method of detecting a V600 polymorphism according to the present invention may be employed as a method of detecting a V600 polymorphism in the BRAF gene, and may include the below-described processes or steps (I) to (IV), and may include the below-described step (V). The method of detecting a polymorphism according to the present invention has the feature of using the above-described probe, and other configurations, conditions and the like are not particularly limited by the description below.

Step (I): contacting the fluorescently-labeled probe with a single-stranded nucleic acid in a sample, to obtain a hybrid.

Step (II): dissociating the hybrid by changing the temperature of the sample containing the hybrid, and measuring the change in fluorescence signal due to the dissociation of the hybrid.

Step (III): measuring the Tm value, which is the dissociation temperature of the hybrid, based on the change in fluorescence signal.

Step (IV): detecting the presence of a V600 polymorphism in the BRAF gene on the single-stranded nucleic acid in the sample, based on the Tm value.

Step (V): determining the abundance ratio of the single-stranded nucleic acid having the polymorphism in the total single-stranded nucleic acids contained in the sample, based on the presence of the polymorphism(s).

Furthermore, the method according to the present invention may further include amplifying the nucleic acid before obtaining the hybrid in step (I) or simultaneously with obtaining the hybrid in step (I), in addition to steps (I) to (IV) or in addition to steps (I) to (V).

The measurement of the Tm value in step (III) may include not only measuring the dissociation temperature of the hybrid, but also measuring the differential values of the fluorescence signal that changes according to the temperature when the hybrid is melted.

In the present invention, the nucleic acid in the sample may be a single-stranded nucleic acid or a double-stranded nucleic acid. In the case in which the nucleic acid is a double-stranded nucleic acid, the method may include, for example, melting (dissociating) the double-stranded nucleic acid in the sample into single-stranded nucleic acids by heating before being hybridized with the fluorescently-labeled probe. The dissociation of a double-stranded nucleic acid into single-stranded nucleic acids enables hybridization with the fluorescently-labeled probe.

In the present invention, the nucleic acid contained in the sample to be detected may be, for example, a nucleic acid originally contained in a biological sample, or an amplification product obtained by amplifying a region of the gene of interest that contains a mutated site(s) of the BRAF gene by PCR or the like using a nucleic acid originally contained in a biological sample as a template with a view to improving the detection accuracy. The length of the amplification product is not particularly limited, and may be, for example, a length from 50 mer to 1,000 mer, or a length from 80 mer to 200 mer. Furthermore, the nucleic acid in the sample may be, for example, a cDNA that has been synthesized from RNAs derived from a biological sample (e.g., total RNAs, mRNAs, etc.) by RT-PCR (Reverse Transcription PCR).

In the present invention, the addition ratio (molar ratio) of the probe according to the present invention relative to the nucleic acids in the sample is not particularly limited. The amount of the probe to be added may be, for example, no more than 1-fold (by mol) of the amount of DNA in the sample. From the viewpoint of ensuring a sufficient detection signal, the addition ratio of the probe according to the present invention to be added relative to the nucleic acids in the sample (in a molar ratio) may be 0.1 or lower.

The "nucleic acids in the sample" may be, for example, the total nucleic acids to be detected that have the polymorphism to be detected and nucleic acids, other than the nucleic acids to be detected, that do not have the polymorphism, or the total amplification products containing a detection target sequence having the polymorphism to be detected and amplification products containing a sequence, other than the detection target sequence, that does not have the polymorphism. Although the ratio of the nucleic acid to be detected relative to nucleic acids in the sample is usually unknown in advance, the consequent addition ratio of the probe relative to the nucleic acids to be detected (or the amplification products containing a sequence to be detected) (in a molar ratio) may be 10 or lower. The addition ratio of the probe relative to the nucleic acids to be detected (or the amplification products containing a sequence to be detected) (in a molar ratio) may be 5 or lower, or 3 or lower. The lower limit of the ratio is not particularly limited, and may be, for example, 0.001 or higher, 0.01 or higher, or 0.1 or higher.

The above-described addition ratio of the fluorescently-labeled probe according to the present invention relative to the DNA may be, for example, a molar ratio relative to the double-stranded nucleic acids or a molar ratio relative to the single-stranded nucleic acids.

In the present invention, the measurement of the change in the signal caused by a temperature change for determining a Tm value may be carried out by measuring the absorbance at 260 nm on the basis of the principle described above. However, the measurement may be carried out by measuring a signal which is based on a signal from the label attached to the fluorescently-labeled probe, and which varies in accordance with the degree of formation of a hybrid of a single-stranded DNA and the probe. Therefore, the above-described fluorescently-labeled oligonucleotide may be used as the fluorescently-labeled probe. Examples of the fluorescently-labeled oligonucleotide (hereinafter sometimes collectively referred to as "fluorescently-labeled oligonucleotide") include a fluorescently-labeled oligonucleotide in respect of which the fluorescence intensity when the oligonucleotide is hybridized with a target sequence thereof is decreased (quenched) as compared to the fluorescence intensity when the oligonucleotide is not hybridized with the target sequence thereof, and a fluorescently-labeled oligonucleotide in respect of which the fluorescence intensity when the oligonucleotide is hybridized with a target sequence thereof is increased as compared to the fluorescence intensity when the oligonucleotide is not hybridized with the target sequence thereof.

The former fluorescently-labeled oligonucleotide does not show a fluorescence signal or only a weak fluorescence signal when the fluorescently-labeled oligonucleotide forms a hybrid (a double-stranded DNA) with the sequence to be detected; however, the fluorescently-labeled oligonucleotide shows a fluorescence signal or shows an increased fluorescence signal when the fluorescently-labeled oligonucleotide is dissociated by heating.

The latter fluorescently-labeled oligonucleotide shows a fluorescence signal when the fluorescently-labeled oligonucleotide forms a hybrid (a double-stranded DNA) with the sequence to be detected; however, the fluorescently-labeled oligonucleotide shows a decreased fluorescence signal or ceases to show a fluorescent signal when the fluorescently-labeled oligonucleotide is dissociated by heating. Therefore, similar to the measurement of the absorbance at 260 nm described above, the progress of melting can be monitored, and the Tm value can be determined by detecting the change in fluorescence signal from the fluorescent label under the conditions specific to the fluorescent label (for example, the fluorescence wavelength thereof).

The method for detecting the change in signal based on a signal from the fluorescent dye in the polymorphism detection method according to the present invention is described below by way of specific examples. The polymorphism detection method according to the present invention has as a feature the use of the fluorescently-labeled polymorphism detection probe, and other processes and conditions of the method are not limited in any way.

The sample containing a nucleic acid that serves as a template for nucleic acid amplification is not particularly limited as long as the sample contains a nucleic acid, particularly the BRAF gene. Examples of such a sample include a sample that is derived from or can be derived from any biological source, examples of which include: a tissue such as colon or lung; a hemocyte such as a leukocyte cell; whole blood; plasma; sputum; a suspension of oral mucosa; a somatic cell of nail, hair or the like; a germ cell; milk; ascitic fluid; a paraffin-embedded tissue; gastric juice; gastric lavage fluid; urine; peritoneal fluid; amniotic fluid; and a cell culture. The method for sampling the sample, the method for preparing the sample containing a nucleic acid, and the like are not limited, and, conventional methods known in the art may be employed therefor. A nucleic acid obtained from such a biological source may be directly used as the template, or may be used after the sample has been subjected to pretreatment that modifies the properties of the sample.

For example, in the case in which whole blood is used as the sample, the isolation of genomic DNA from the whole blood may be carried out by a conventional method known in the art. For example, a commercially available genomic DNA isolation kit (trade name: GFX GENOMIC BLOOD DNA PURIFICATION KIT, available from GE Healthcare Biosciences), etc. may be used.

Next, a fluorescently-labeled polymorphism detection probe including the fluorescently-labeled oligonucleotide is added to the sample containing the isolated genomic DNA.

The fluorescently-labeled probe may be added to a liquid sample containing the isolated genomic DNA, or may be mixed with the genomic DNA in an appropriate solvent. The solvent is not particularly limited, and examples of the solvent include conventional solvents known in the art, such as: a buffer solution such as Tris-HCl; a solvent containing at least one of KCl, $MgCl_2$, $MgSO_4$, or glycerol; and a PCR reaction solution.

The timing of the addition of the fluorescently-labeled probe is not particularly limited. For example, in the case in which an amplification process such as PCR described below is carried out, the fluorescently-labeled probe may be added to the PCR amplification products after the amplification process is carried out, or may be added before the amplification process is carried out.

In the case in which the fluorescently-labeled probe is added before an amplification process such as PCR is carried out, for example, a fluorescent dye or a phosphate group may have been added to the 3' end of the probe, as described above.

The method of amplifying a nucleic acid may be, for example, a method in which a polymerase is employed. Examples thereof include a PCR method, an ICAN method, a LAMP method, and an NASBA method. In the case in which the amplification is carried out by a method in which a polymerase is employed, the amplification may be carried out in the presence of the fluorescently-labeled probe according to the present invention. Those skilled in the art would be able to easily adjust the reaction conditions of the amplification and the like in accordance with the fluorescently-labeled probe and the polymerase to be used. In the case in which the amplification is carried out in the presence of the fluorescently-labeled probe according to the present invention, a polymorphism can be detected by analyzing the Tm value of the fluorescently-labeled probe only after the amplification of the nucleic acid is carried out, and, therefore, it is not necessary to separate the amplification product after completion of the reaction. Thus, contamination by (or of) the amplification product does not occur. In addition, since the detection can be carried out by the same apparatus as the apparatus required for the amplification, conveyance of a vessel is unnecessary, and automatization of the process is facilitated.

The DNA polymerase to be used in the PCR method may be selected, without particular limitation, from DNA polymerases that are usually used for PCR. Examples of the DNA polymerase include GENE TAQ (trade name, manufactured by NIPPON GENE CO., LTD.), PRIMESTAR MAX DNA POLYMERASE (trade name, manufactured by Takara Bio Inc.), and a Taq polymerase.

The amount of the polymerase to be used is not particularly limited as long as a usually-applied polymerase concentration is provided. For example, in the case in which a Taq polymerase is used, the concentration of the Taq polymerase may be, for example, a concentration from 0.01 U to 100 U relative to 50 µl of the reaction solution. In this range, for example, the sensitivity of the detection of the V600 polymorphism in the BRAF gene tends to be increased.

The PCR method may be carried out under the conditions appropriately selected from usually-employed conditions.

When the amplification is carried out, the amplification may be monitored using real-time PCR so that the copy number of the DNA (a sequence to be detected) contained in the sample can be measured. In other words, the proportion of probes forming hybrids is increased as the amplification of the DNA (a sequence to be detected) by PCR proceeds, thereby changing the fluorescence intensity. By monitoring the change in fluorescence intensity, the copy number and/or the abundance ratio of the sequence to be detected (either a normal DNA or a mutant DNA) contained in the sample can be obtained.

In the polymorphism detection method according to the present invention, the fluorescently-labeled oligonucleotide and a single-stranded nucleic acid in the sample are brought into contact with each other, thereby allowing hybridization to occur. The single-stranded nucleic acid in the sample can be prepared by, for example, dissociating the PCR amplification products obtained in the above-described manner.

The heating temperature employed for dissociation of the PCR amplification products (the heating temperature in the dissociation process) is not particularly limited as long as it is a temperature at which the amplification products can be dissociated. For example, the heating temperature may be in the range from 85° C. to 95° C. The heating time is not particularly limited, either. The heating time may be, for example, in the range from 1 second to 10 minutes, or from 1 second to 5 minutes.

The hybridization of the dissociated single-stranded DNA and the fluorescently-labeled oligonucleotide may be carried out by, for example, decreasing, after the dissociation process, the temperature from the heating temperature employed in the dissociation process. The temperature condition for the hybridization may be, for example, in the range from 40° C. to 50° C.

The volume and concentration of each component in the reaction solution in the hybridization process are not particularly limited. In regard to specific examples thereof, the concentration of DNA in the reaction solution may be, for example, a concentration from 0.01 µM to 1 µM, or a concentration from 0.1 µM to 0.5 µM. The concentration of the fluorescently-labeled oligonucleotide may be, for example, in a range in which the above-described addition ratio relative to the DNA is satisfied, and may be, for example, a concentration from 0.001 µM to 10 µM, or a concentration from 0.001 µM to 1 µM.

The resultant hybrid of the single-stranded DNA and the fluorescently-labeled oligonucleotide is gradually heated, and the change in fluorescence signal caused by the temperature increase is measured. For example, in the case of using Q PROBE®, the fluorescence intensity when the probe is hybridized with the single-stranded DNA is decreased (or quenched) as compared to the fluorescence intensity in the dissociated state. Therefore, for example, the hybrid emitting decreased fluorescence or the quenched hybrid may be gradually heated, and the increase in fluorescence intensity caused by the temperature increase may be measured.

The temperature range in which the change in fluorescence intensity is measured is not particularly limited, and the initial temperature may be, for example, a temperature from room temperature to 85° C., or a temperature from 25° C. to 70° C. The final temperature may be, for example, a temperature from 40° C. to 105° C. The rate of temperature increase is not particularly limited, either, and may be, for example, in the range from 0.1° C./sec to 20° C./sec, or in the range from 0.3° C./sec to 5° C./sec.

Next, the change in signal is analyzed to determine the Tm value. More specifically, the Tm value may be determined by calculating a differential value at each temperature (−d(Fluorescence Intensity)/dt) from the fluorescence intensity obtained, and taking the temperature at which the differential value has the lowest value as the Tm value. The Tm value may alternatively be determined as the point at which the increase in fluorescence intensity per unit time ((Increase in Fluorescence Intensity)/t) has the largest value. On the contrary, in the case in which a probe in relation to which the signal intensity is increased by the formation of the hybrid, rather than a quenching probe, is used as the fluorescently-labeled probe, the signal analysis and the determination of the Tm value may be carried out by measuring the decrease in fluorescence intensity.

In the present invention, the change in fluorescence signal caused by the temperature increase (preferably an increase in fluorescence intensity) may be measured while heating the hybrid as described above. However, instead of this method, the measurement of the change in signal may alternatively be carried out, for example, during the course of hybrid formation. In other words, the temperature of the sample, to which the probe has been added, may be decreased, and the change in fluorescence signal caused by the temperature decrease may be measured during the course of hybrid formation.

For example, in the case in which Q PROBE® is used, the fluorescence intensity is high when the probe is added to the sample since the probe is in the dissociated state. However, when the hybrid is formed by a decrease in temperature, the fluorescence is decreased (or quenched). Therefore, for example, a decrease in fluorescence intensity caused by the temperature decrease may be measured while gradually decreasing the temperature of the heated sample.

On the other hand, in the case in which a probe in relation to which the signal therefrom is increased by hybrid formation is used, the fluorescence intensity is low (or quenched) when the probe is added to the sample since the probe is in the dissociated state. However, when the hybrid is formed by a decrease in temperature, the fluorescence intensity is increased. Therefore, for example, the increase in fluorescence intensity caused by the temperature decrease may be measured while gradually decreasing the temperature of the sample.

<Method of Evaluating Drug Efficacy>

The method of evaluating the efficacy of a drug according to the present invention includes detecting a polymorphism in the BRAF gene by the above-described polymorphism detection method; and evaluating tolerance to a therapeutic agent or the efficacy of a therapeutic agent based on the results of the detection.

In the above-described method of detecting a V600 polymorphism, a polymorphism in the BRAF gene is detected easily with high sensitivity by using the polymorphism detection probe according to the present invention; therefore, based on this polymorphism in the BRAF gene, a therapeutic agent can be evaluated easily with high sensitivity.

In addition, the tolerance to a therapeutic agent and its efficacy can be evaluated based on the presence or absence of a polymorphism and the abundance ratio of a mutant sequence and/or a normal sequence. Furthermore, the method of evaluating the efficacy of a therapeutic agent according to the present invention is useful in determining whether a therapeutic strategy should be changed by, for example, increasing the dosage of the therapeutic agent or using a different therapeutic agent, based on the presence or absence of a mutation and the abundance ratio of a mutant sequence.

Here, specific examples of the drug to be evaluated include molecular-targeted therapeutic agents, malignant melanoma drugs and anticancer agents, and in particular, the drug to be evaluated may be a molecular-targeted therapeutic agent or a malignant melanoma drug.

<Reagent Kit for Detecting Polymorphism>

The reagent kit (also referred to herein as a kit) for detecting a V600 polymorphism in the BRAF gene according to the present invention includes the above-described polymorphism detection probe(s).

This reagent kit for detecting a polymorphism includes at least one of the above-described polymorphism detection probes capable of easily detecting, in the BRAF gene, a polymorphism in the bases corresponding to the 228th to the 230th bases of the base sequence indicated in SEQ ID NO:1 with high sensitivity; therefore, for example, the reagent kit is able to detect a V600 polymorphism in the BRAF gene more easily.

In addition, the reagent kit for detecting a polymorphism according to the present invention may also include a primer for amplifying a base sequence containing the above-described BRAF gene polymorphism(s) to be detected. This enables the reagent kit for detecting a V600 polymorphism according to the present invention to detect a polymorphism in the BRAF gene with good accuracy.

Further, the reagent kit for detecting a polymorphism according to the present invention may further contain a primer which is capable of performing amplification using, as a template, a region having a length of 50 to 1,000 bases including the 228th to the 230th bases of the base sequence indicated in SEQ ID NO:1.

Here, with regard to the probe and primer that may be included in the reagent kit for detecting a polymorphism, those matters described above can be applied as they are.

In a case in which two or more types of fluorescently-labeled oligonucleotide are contained as the probes, the oligonucleotides may be contained as a mixture, or may be contained separately.

Further, in cases where the reagent kit for detecting a polymorphism according to the present invention contains a mixture of two or more types of the probes according to the present invention or in cases where the reagent kit for detecting a polymorphism contains the probes as separate reagents but, for example, these probes are used in the same reaction system to perform Tm analysis with the respective fluorescently labeled oligonucleotides and the sequences to be detected, it is preferred that the two or more types of the probes are each labeled with a fluorescent dye having a different emission wavelength.

By using probes labeled with respectively different fluorescent dyes, detection of the signal from each fluorescently-labeled oligonucleotide can simultaneously be carried out even in a single reaction system.

Besides the probe, the reagent kit according to the present invention may further include reagents required for carrying out nucleic acid amplification in the detection method according to the present invention. The probe, the primers and other reagents may be separately contained, or some of them may be contained as a mixture.

The term "separately contained" may refer to a state in which individual reagents are separated from each other such that the non-contact state therebetween is maintained, and does not necessarily require that the individual reagents be contained in separate containers that can be independently handled.

When the reagent kit includes a primer set for amplifying a base sequence including a base at the polymorphism site (a region to which the probe can hybridize), detection of the polymorphism with higher sensitivity, for example, can be achieved.

The reagent kit according to the present invention may further include an instruction manual that provides instructions for the generation of a differential melting curve for a sample containing a nucleic acid to be detected using the probe, and for the detection of a V600 polymorphism in the BRAF gene through Tm value analysis based on the differential melting curve, or instructions that describe various reagents that are contained, or may additionally be contained, in the reagent kit.

EXAMPLES

The present invention will now be described in detail by way of examples. However, the present invention is not limited to these examples in any way.

Example 1, Example 2 and Comparative Example 1

Using a fully-automated SNP analyzer (trade name: I-DENSY (trademark); manufactured by ARKRAY, Inc.), a sample shown in Table 4 below (artificial nucleic acid mixture 1 μL/reaction solution) and a PCR solution shown in Table 5 below were subjected to PCR and Tm analysis. In the samples shown in Table 4, the wild-type plasmid indicated in SEQ ID NO:2, the V600E plasmid indicated in SEQ ID NO:3, the V600K plasmid indicated in SEQ ID NO:4, the V600R plasmid indicated in SEQ ID NO:5 and V600D plasmid indicated in SEQ ID NO:6 were each used.

TABLE 4

| Sample: Copy number of each plasmid in 1 μL of nucleic acid mixture: | | |
|---|---|---|
| Mutation content | WT sample | mt sample |
| WT | 10,000 | 0 |
| mt 10% | 9,000 | 1,000 |
| mt 5% | 9,500 | 500 |

TABLE 5

| PCR solution In 50 μL of PCR solution: | |
|---|---|
| Taq polymerase | 1.88 U |
| Tris-HCl | 25 mmol/L |
| BSA | 0.20% |
| Glycerol | 4.50% |
| KCl | 45 mmol/L |
| MgCl2 | 1.5 mmol/L |
| dNTP | 0.2 mmol/L |
| BRAF-F3 | 0.3 μmol/L |
| BRAF-R5 | 1.5 μmol/L |
| Probe | 0.1 μmol/L |

The details of the probes and primers that were used in the above Table 5 are shown in Tables 6 and 7, respectively. In the parentheses at the 3'-end of each probe, the type of the fluorescent dye is indicated.

TABLE 6

| name | | sequence (5'→3') | mer | SEQ ID NO: |
|---|---|---|---|---|
| Example 1 | 3PB-BRAF600KDmt-F1-21 | gtctagctacaAATaaatctc-(PB) | 21 | 8 |
| Example 2 | 3FL-BRAF600Rmt-F1-18 | tagctacaAGgaaatctc-(FL) | 18 | 9 |
| Comparative Example 1 | 3T-BRAF600Emt-F1-16 | gctacagAgaaatctc-(TAMRA) | 16 | 7 |

TABLE 7

| name | sequence (5'→3') | mer | SEQ ID NO: |
|---|---|---|---|
| BRAF-F3 | tgcttgctctgataggaaaatgagatctac | 30 | 17 |
| BRAF-R5 | aaactgatgggacccactccat | 22 | 18 |

PCR was performed by treating the reaction solution at 95° C. for 60 seconds and then repeating 50 cycles of 95° C. for 1 second and 58° C. for 15 seconds.

The Tm analysis was performed after the PCR by treating the reaction solution at 95° C. for 1 second and then at 40° C. for 60 seconds and subsequently measuring the change in fluorescence intensity over time during a period in which the temperature of the solution was increased from 40° C. to 75° C. at a rate of 1° C./3 seconds.

It is noted here that the fluorescent dye, PACIFIC BLUE, has an excitation wavelength of 365 nm to 415 nm and a detection wavelength of 445 nm to 480 nm. The fluorescent dye, BODIPY FL, has an excitation wavelength of 420 nm to 485 nm and a detection wavelength of 520 nm to 555 nm, and the fluorescent dye, TAMRA, has an excitation wavelength of 520 nm to 555 nm and a detection wavelength of 585 nm to 700 nm. Based on these wavelengths, the changes in fluorescence intensity originating from the respective fluorescently labeled probes were measured.

The Tm analysis yielded FIG. 2 and FIG. 3 showing the changes in the fluorescence value of the respective probes.

In FIG. 2, the graphs (A) to (E) show the results obtained by using the probe indicated in SEQ ID NO:8 and the graphs (F) to (J) show the results obtained by using the probe indicated in SEQ ID NO:7.

In FIG. 2, graphs (A) and (F) show the results obtained by using the wild-type plasmid as the sample, graphs (B) and (G) show the results obtained by using the V600E plasmid (mt 5%) as the sample, graphs (C) and (H) show the results obtained by using the V600K plasmid (mt 5%) as the sample, graphs (D) and (I) show the results obtained by using the V600R plasmid (mt 5%) as the sample, and graphs (E) and (J) show the results obtained by using the V600D plasmid (mt 5%) as the sample.

In FIG. 3, the graphs (A) to (E) show the results obtained by using the probe indicated in SEQ ID NO:9 and the graphs (F) to (J) show the results obtained by using the probe indicated in SEQ ID NO:7.

In FIG. 3, graphs (A) and (F) show the results obtained by using the wild-type plasmid as the sample, graphs (B) and (G) show the results obtained by using the V600E plasmid (mt 10%) as the sample, graphs (C) and (H) show the results obtained by using the V600K plasmid (mt 10%) as the sample, graphs (D) and (I) show the results obtained by using the V600R plasmid (mt 10%) as the sample, and graphs (E) and (J) show the results obtained by using the V600D plasmid (mt 10%) as the sample.

In FIGS. 2 and 3, the ordinate indicates the change in the fluorescence intensity per unit time (increase in the d-fluorescence intensity/t) and the abscissa indicates the temperature (° C.).

In FIG. 2(C), in addition to the peak at about 43° C. which was observed for the wild-type sample in FIG. 2(A), there was also another peak observed at 51° C. Further, in FIG. 2(E), in addition to the peak at about 43° C., there was also another peak observed at 49° C.

From these results, it was demonstrated that two mutations of V600K and V600D can be simultaneously detected by using the probe indicated in SEQ ID NO:8, which is a polymorphism detection probe according to the present invention.

Meanwhile, as clearly seen from the results of FIGS. 2(F) to (J), when the probe indicated in SEQ ID NO:7 was used, only the V600E mutation was detected.

In FIG. 3(C), in addition to the peak at about 45° C. which was observed for the wild-type sample in FIG. 3(A), there was also another peak observed at 49° C. Further, in FIG. 3(D), in addition to the peak at about 45° C., there was also another peak observed at 57° C.

From these results, it was demonstrated that two mutations of V600K and V600R can be simultaneously detected by using the probe indicated in SEQ ID NO:9, which is a polymorphism detection probe according to the present invention.

Meanwhile, as clearly seen from the results of FIGS. 3(F) to (J), when the probe indicated in SEQ ID NO:7 was used, only the V600E mutation was detected.

Comparative Example 2

Tm analysis was performed in the same manner as in Example 1, except that the polymorphism detection probe was changed to the probes of SEQ ID NOs:14 to 16 shown in Table 8 below.

TABLE 8

| name | sequence (5'→3') | mer | SEQ ID NO: |
|---|---|---|---|
| 3FL-BRAF600WT-F1-19 | ctagctacagTgaaatctc-(FL) | 19 | 14 |
| 3FL-BRAF600WT-F2-29 | tgattttggtctagctacagTgaaatctc-(FL) | 29 | 15 |
| 3FL-BRAF600WT-F3-24 | ttggtctagctacagTgaaatctc-(FL) | 24 | 16 |

As a result, FIG. 4 showing the changes in the fluorescence value of the respective probes was obtained. In FIG. 4, the ordinate indicates the change in the fluorescence intensity per unit time (increase in the d-fluorescence intensity/t) and the abscissa indicates the temperature (° C.).

In FIG. 4, graphs (A) to (E) show the results obtained by using the probe indicated in SEQ ID NO:10, graphs (F) to (J) show the results obtained by using the probe indicated in SEQ ID NO:11, and graphs (K) to (0) show the results obtained by using the probe indicated in SEQ ID NO:12.

In FIG. 4, graphs (A), (F) and (K) show the results obtained by using the wild-type plasmid as the sample, graphs (B), (G) and (L) show the results obtained by using the V600E plasmid (mt 10%) as the sample, graphs (C), (H) and (M) show the results obtained by using the V600K plasmid (mt 10%) as the sample, graphs (D), (I) and (N) show the results obtained by using the V600R plasmid (mt 10%) as the sample, and graphs (E), (J) and (0) show the results obtained by using the V600D plasmid (mt 10%) as the sample.

As seen from the results shown in FIGS. 4(A) to (O), it was demonstrated that, with the use of the probes of SEQ ID NO:14 to 16, a V600 mutation in the BRAF gene cannot be detected.

From the above-described results, it was demonstrated that, by the present invention, a V600 polymorphism in the BRAF gene can be detected easily with high sensitivity.

[Sequence Listing]

The invention claimed is:

1. A probe consisting of a fluorescently labeled oligonucleotide having a nucleotide sequence consisting of SEQ ID NO: 8 or 9,
wherein the fluorescently labeled oligonucleotide is labeled with a fluorescent dye at the 3'-end.

2. The probe according to claim 1, wherein the fluorescence intensity of the fluorescently labeled oligonucleotide when hybridized to a target sequence is decreased or increased as compared to when not hybridized to the target sequence.

3. The probe according to claim 1, wherein the fluorescence intensity of the fluorescently labeled oligonucleotide when hybridized to the target sequence is decreased as compared to when not hybridized to the target sequence.

4. The probe according to claim 1, being a probe for melting curve analysis.

5. A method of detecting a polymorphism at the V600 locus of the BRAF gene, which comprising using the probe according to claim 1.

6. The method according to claim 5, comprising the steps of:

(I) bringing the probe according to claim 1 into contact with a single-stranded nucleic acid contained in a sample to allow hybridization of said fluorescently labeled oligonucleotide to the single-stranded nucleic acid, thereby obtaining a hybrid;

(II) dissociating the hybrid by changing the temperature of the sample containing the hybrid to measure a change in the fluorescence signal caused by dissociation of the hybrid;

(III) determining the Tm value, which is the dissociation temperature of the hybrid, based on the change in fluorescence signal; and (IV) based on the Tm value, detecting the presence of a mutation at the V600 locus of the BRAF gene.

7. The method according to claim 5, further comprising amplifying the nucleic acid prior to or simultaneously with obtaining the hybrid.

8. A method of evaluating the efficacy of a drug, comprising the steps of: detecting a mutation at the V600 locus of the BRAF gene by the method according to claim 5; and determining tolerance to the drug or the efficacy of the drug based on the presence or absence of a detected mutation, wherein said drug is selected from a molecular-targeted therapeutic agent, a malignant melanoma drug and an anticancer agent.

9. A reagent for detecting a polymorphism, the reagent comprising the probe according to claim 1.

10. A kit for detecting a polymorphism, the kit comprising:
the probe according to claim 1; and
a primer capable of performing amplification using, as a template, a region of the base sequence indicated in SEQ ID NO: 1 that contains a sequence to which the probe hybridizes.

11. The kit according to claim 10, wherein said primer is capable of performing amplification using, as a template, a region having a length of 50 to 1,000 bases including the 228th to the 230th bases of the base sequence indicated in SEQ ID NO: 1.

12. The probe according to claim 1, wherein the fluorescently labeled oligonucleotide has the nucleotide sequence consisting of SEQ ID NO: 8.

13. The probe according to claim 1, wherein the fluorescently labeled oligonucleotide has the nucleotide sequence consisting of SEQ ID NO: 9.

\* \* \* \* \*

```
SEQUENCE LISTING

<160> NUMBER OF SEQ ID NOS: 19

<210> SEQ ID NO 1
<211> LENGTH: 500
<212> TYPE: DNA
<213> ORGANISM: Homo sapiens

<400> SEQUENCE: 1
tcattgtttt agacatactt attgactcta agaggaaaga tgaagtacta tgttttaaag      60
aatattatat tacagaatta tagaaattag atctcttacc taaactcttc ataatgcttg     120
ctctgatagg aaaatgagat ctactgtttt cctttactta ctacacctca gatatatttc     180
ttcatgaaga cctcacagta aaaataggtg attttggtct agctacagtg aaatctcgat     240
ggagtgggtc ccatcagttt gaacagttgt ctggatccat tttgtggatg gtaagaattg     300
aggctatttt tccactgatt aaattttttgg ccctgagatg ctgctgagtt actagaaagt     360
cattgaaggt ctcaactata gtatttcat agttcccagt attcacaaaa atcagtgttc      420
ttatttttta tgtaaataga ttttttaact tttttcttta cccttaaaac gaatattttg     480
aaaccagttt cagtgtattt                                                 500

<210> SEQ ID NO 2
<211> LENGTH: 300
<212> TYPE: DNA
<213> ORGANISM: Artificial
<220> FEATURE:
<223> OTHER INFORMATION: wild type plasmid

<400> SEQUENCE: 2
tgttttaaag aatattatat tacagaatta tagaaattag atctcttacc taaactcttc      60
ataatgcttg ctctgatagg aaaatgagat ctactgtttt cctttactta ctacacctca    120
gatatatttc ttcatgaaga cctcacagta aaaataggtg attttggtct agctacagtg    180
aaatctcgat ggagtgggtc ccatcagttt gaacagttgt ctggatccat tttgtggatg    240
gtaagaattg aggctatttt tccactgatt aaattttttgg ccctgagatg ctgctgagtt    300

<210> SEQ ID NO 3
<211> LENGTH: 300
<212> TYPE: DNA
<213> ORGANISM: Artificial
<220> FEATURE:
<223> OTHER INFORMATION: V600E plasmid

<400> SEQUENCE: 3
tgttttaaag aatattatat tacagaatta tagaaattag atctcttacc taaactcttc      60
ataatgcttg ctctgatagg aaaatgagat ctactgtttt cctttactta ctacacctca    120
```

```
gatatatttc ttcatgaaga cctcacagta aaaataggtg attttggtct agctacagag    180
aaatctcgat ggagtgggtc ccatcagttt gaacagttgt ctggatccat tttgtggatg    240
gtaagaattg aggctatttt tccactgatt aaattttggg ccctgagatg ctgctgagtt    300
```

```
<210> SEQ ID NO 4
<211> LENGTH: 300
<212> TYPE: DNA
<213> ORGANISM: Artificial
<220> FEATURE:
<223> OTHER INFORMATION: V600K plasmid

<400> SEQUENCE: 4
tgttttaaag aatattatat tacagaatta tagaaattag atctcttacc taaactcttc     60
ataatgcttg ctctgatagg aaaatgagat ctactgtttt cctttactta ctacacctca    120
gatatatttc ttcatgaaga cctcacagta aaaataggtg attttggtct agctacaaag    180
aaatctcgat ggagtgggtc ccatcagttt gaacagttgt ctggatccat tttgtggatg    240
gtaagaattg aggctatttt tccactgatt aaattttggg ccctgagatg ctgctgagtt    300
```

```
<210> SEQ ID NO 5
<211> LENGTH: 300
<212> TYPE: DNA
<213> ORGANISM: Artificial
<220> FEATURE:
<223> OTHER INFORMATION: V600R plasmid

<400> SEQUENCE: 5
tgttttaaag aatattatat tacagaatta tagaaattag atctcttacc taaactcttc     60
ataatgcttg ctctgatagg aaaatgagat ctactgtttt cctttactta ctacacctca    120
gatatatttc ttcatgaaga cctcacagta aaaataggtg attttggtct agctacaagg    180
aaatctcgat ggagtgggtc ccatcagttt gaacagttgt ctggatccat tttgtggatg    240
gtaagaattg aggctatttt tccactgatt aaattttggg ccctgagatg ctgctgagtt    300
```

```
<210> SEQ ID NO 6
<211> LENGTH: 300
<212> TYPE: DNA
<213> ORGANISM: Artificial
<220> FEATURE:
<223> OTHER INFORMATION: V600D plasmid

<400> SEQUENCE: 6
tgttttaaag aatattatat tacagaatta tagaaattag atctcttacc taaactcttc     60
ataatgcttg ctctgatagg aaaatgagat ctactgtttt cctttactta ctacacctca    120
gatatatttc ttcatgaaga cctcacagta aaaataggtg attttggtct agctacagat    180
aaatctcgat ggagtgggtc ccatcagttt gaacagttgt ctggatccat tttgtggatg    240
gtaagaattg aggctatttt tccactgatt aaattttggg ccctgagatg ctgctgagtt    300
```

```
<210> SEQ ID NO 7
<211> LENGTH: 16
<212> TYPE: DNA
<213> ORGANISM: Artificial
<220> FEATURE:
<223> OTHER INFORMATION: probe

<400> SEQUENCE: 7
gctacagaga aatctc                                                     16
```

<210> SEQ ID NO 8
<211> LENGTH: 21
<212> TYPE: DNA
<213> ORGANISM: Artificial
<220> FEATURE:
<223> OTHER INFORMATION: probe

<400> SEQUENCE: 8
gtctagctac aaataaatct c                                              21

<210> SEQ ID NO 9
<211> LENGTH: 18
<212> TYPE: DNA
<213> ORGANISM: Artificial
<220> FEATURE:
<223> OTHER INFORMATION: probe

<400> SEQUENCE: 9
tagctacaag gaaatctc                                                  18

<210> SEQ ID NO 10
<211> LENGTH: 32
<212> TYPE: DNA
<213> ORGANISM: Artificial
<220> FEATURE:
<223> OTHER INFORMATION: probe

<400> SEQUENCE: 10
aggtgatttt ggtctagcta caaataaatc tc                                  32

<210> SEQ ID NO 11
<211> LENGTH: 15
<212> TYPE: DNA
<213> ORGANISM: Artificial
<220> FEATURE:
<223> OTHER INFORMATION: probe

<400> SEQUENCE: 11
ctacaaataa atctc                                                     15

<210> SEQ ID NO 12
<211> LENGTH: 29
<212> TYPE: DNA
<213> ORGANISM: Artificial
<220> FEATURE:
<223> OTHER INFORMATION: probe

<400> SEQUENCE: 12
tgattttggt ctagctacaa ggaaatctc                                      29

<210> SEQ ID NO 13
<211> LENGTH: 15
<212> TYPE: DNA
<213> ORGANISM: Artificial
<220> FEATURE:
<223> OTHER INFORMATION: probe

<400> SEQUENCE: 13
ctacaaggaa atctc                                                     15

<210> SEQ ID NO 14
<211> LENGTH: 19
<212> TYPE: DNA
<213> ORGANISM: Artificial
<220> FEATURE:
<223> OTHER INFORMATION: probe

```
<400> SEQUENCE: 14
ctagctacag tgaaatctc                                                    19

<210> SEQ ID NO 15
<211> LENGTH: 29
<212> TYPE: DNA
<213> ORGANISM: Artificial
<220> FEATURE:
<223> OTHER INFORMATION: probe

<400> SEQUENCE: 15
tgattttggt ctagctacag tgaaatctc                                         29

<210> SEQ ID NO 16
<211> LENGTH: 24
<212> TYPE: DNA
<213> ORGANISM: Artificial
<220> FEATURE:
<223> OTHER INFORMATION: probe

<400> SEQUENCE: 16
ttggtctagc tacagtgaaa tctc                                              24

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tgcttgctct gataggaaaa tgagatctac                                        30

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
aaactgatgg gacccactcc at                                                22

<210> SEQ ID NO 19
<211> LENGTH: 19
<212> TYPE: DNA
<213> ORGANISM: Artificial
<220> FEATURE:
<223> OTHER INFORMATION: probe

<400> SEQUENCE: 19
ctagctacag agaaatctc                                                    19
```